(12) United States Patent
Debold

(10) Patent No.: US 9,649,177 B2
(45) Date of Patent: May 16, 2017

(54) DENTAL IMPLANT SET

(71) Applicant: Martin Debold, Sprockhövel (DE)

(72) Inventor: Martin Debold, Sprockhövel (DE)

( * ) Notice: Subject to any disclaimer, the term of this patent is extended or adjusted under 35 U.S.C. 154(b) by 128 days.

(21) Appl. No.: 14/428,065

(22) PCT Filed: Sep. 17, 2012

(86) PCT No.: PCT/EP2012/068241
§ 371 (c)(1),
(2) Date: Jul. 13, 2015

(87) PCT Pub. No.: WO2014/040654
PCT Pub. Date: Mar. 20, 2014

(65) Prior Publication Data
US 2015/0305835 A1    Oct. 29, 2015

(51) Int. Cl.
*A61F 2/28* (2006.01)
*A61C 8/02* (2006.01)
*A61C 8/00* (2006.01)
*A61C 3/02* (2006.01)
*A61F 2/30* (2006.01)

(52) U.S. Cl.
CPC ............. *A61C 8/0006* (2013.01); *A61C 3/02* (2013.01); *A61C 8/0089* (2013.01); *A61F 2/2803* (2013.01); *A61F 2/2846* (2013.01); *A61F 2002/302* (2013.01); *A61F 2002/30235* (2013.01); *A61F 2002/30968* (2013.01)

(58) Field of Classification Search
CPC ....... A61C 8/0006; A61C 8/0089; A61C 3/02; A61F 2/2803; A61F 2/2846; A61F 2002/302; A61F 2002/30235; A61F 2002/30968
See application file for complete search history.

(56) References Cited

U.S. PATENT DOCUMENTS

| | | | | |
|---|---|---|---|---|
| 8,690,874 | B2 * | 4/2014 | Thorne | A61K 38/1875 424/423 |
| 8,697,107 | B2 * | 4/2014 | Drapeau | A61K 35/28 424/400 |
| 8,741,267 | B1 * | 6/2014 | Trovato | A61Q 11/00 424/49 |
| 9,132,208 | B2 * | 9/2015 | Chen | A61L 27/3604 |
| 9,168,139 | B2 * | 10/2015 | Zigdon-Giladi | A61L 27/12 |
| 9,308,190 | B2 * | 4/2016 | Li | A61K 31/22 |
| 9,408,875 | B2 * | 8/2016 | Masinaei | A61L 27/3604 |

(Continued)

FOREIGN PATENT DOCUMENTS

| | | |
|---|---|---|
| DE | 35 43 737 A1 | 6/1987 |
| DE | 20 2007 003 035 U1 | 8/2007 |
| DE | 10 2006 037 362 B3 | 9/2007 |

(Continued)

OTHER PUBLICATIONS

International Search Report of PCT/EP2012/068241, mailed Jun. 5, 2013.

*Primary Examiner* — Glenn Richman
(74) *Attorney, Agent, or Firm* — Collard & Roe, P.C.

(57) ABSTRACT

A dental implant set has: an implant, a granular bone substitute material, and a membrane. To provide an implant set of this type, by which the process of augmentation is improved, the bone substitute material and the membrane are of a hard and solid consistency.

22 Claims, 4 Drawing Sheets

(56) References Cited

U.S. PATENT DOCUMENTS

Figure 1:
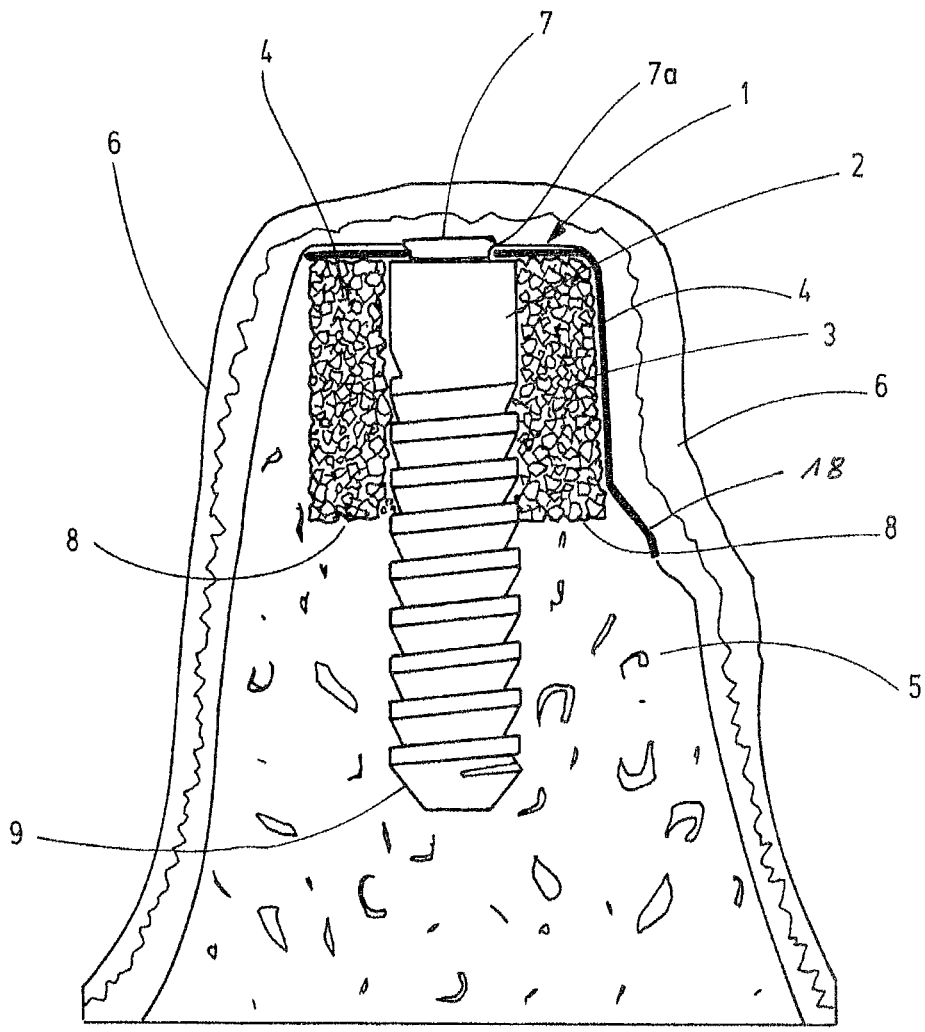

2008/0147197 A1 6/2008 McKay
2009/0254192 A1 10/2009 Park et al.

FOREIGN PATENT DOCUMENTS

DE   10 2009 028 824 A1   3/2011
JP        2002-224141 A    8/2002
WO        2008/017325 A1   2/2008

* cited by examiner

DENTAL IMPLANT SET

CROSS REFERENCE TO RELATED APPLICATIONS

This application is the National Stage of PCT/EP2012/068241 filed on Sep. 17, 2012, the disclosure of which is incorporated by reference. The international application under PCT article 21(2) was not published in English.

The invention relates to a dental implant set in accordance with the preamble of claim 1.

Implants, bone substitute materials, membranes, as well as surgical instruments, particularly implant drills, are used as essential components and instruments within the scope of implant treatment when bone conditions are not optimal.

The cause of these non-optimal bone conditions is often a great distance in time between tooth loss and implantation. As a result, irregular atrophy comes about, in part, i.e. degeneration or degradation of the jaw ridge both in the vertical and in the transversal direction.

For this purpose, before implantation, the bone is first prepared for the planned position and implant size, after the gums have been opened at the planned implant location, by means of an incision or a punch with implant drills. A plurality of implant drills is known from the state of the art.

Then, the degraded parts of the tooth-bearing bone are reconstructed by means of the use of synthetically produced granular bone substitute materials. An example for a granular bone substitute material is evident from DE 10 2006 037 362 B3, which discloses a bone substitute material that contains calcium carbonate.

In this connection, shielding to prevent the invasion of connective tissue, which would prevent osseous regeneration of the defect, is achieved by means of the use of additional membranes. In the state of the art, synthetic polymers, such as polylactides or polyglycolides, as well as their chemical modification, are preferably used as materials for membranes. The membranes are very thin elastic films. A distinction is made between resorbable membranes, which are decomposed by the body and do not have to be removed, and non-resorbable membranes.

Alternatively, the remaining bone defect is filled with synthetic bone substitute material after introduction of the dental implant, and once again provided with a membrane.

The bone substitute materials known from the state of the art possess a granular structure and, depending on the grain size, have the property, after introduction, of being able to be compressed under external pressure, which leads to a non-desired irregularity in the bone structure that finally forms. Such changes in the augmentation structure, i.e. the increase in bone mass, can already be induced by the process of the suture closure of the implantation wound.

Furthermore, the elasticity and plasticity of the membranes currently in use does not offer sufficient protection against external compression during augmentation. The conventionally used membranes currently also do not deliver optimal shielding against invasive connective tissue cells. The sub-periosteal bone thickness required circularly, i.e. situated below the periosteum, around the implant, of 1.5 to 2 mm, is furthermore often not reached within the scope of the use of conventional bone substitute materials in combination with the membrane, and this significantly worsens the prognosis of durability of the implant.

It is therefore the task of the present invention to make available a dental implant set of the type stated initially, the components of which eliminate the disadvantages of the conventional practice of augmentation.

This task is accomplished with the characteristics of claim 1. Advantageous embodiments of the invention are evident from the dependent claims.

The task is accomplished, according to the invention, in that the bone substitute material and the membrane are of a hard and solid consistency.

It is the core idea of the invention to prevent elastic deformation with an accompanying change in volume and increase in density of the bone substitute material and of the membrane by means of an incompressible form of the bone substitute material and of the membrane. A solid and hard state of the granular bone substitute material as well as of the membrane, for example a polylactide, is almost incompressible. The transformation of a granular (granular) material for the bone substitute material into a solid and hard state can take place by means of conventional methods, for example by means of sintering or gluing using fibrin adhesive. The transformation of the membrane into a hard and solid state can also be implemented by means of conventional methods.

After the usual times for healing and osteoregeneration, a defined alveolar bone situation with an optimal bone thickness is advantageously achieved. As a result, additional operative procedures before implantation are eliminated, and this minimizes time and costs.

An advantageous further development of the invention provides that the set has a surface-milling cutter as a surgical instrument. Surface-milling cutters have already found use within the scope of medical treatments, as DE 20 2007 003 035 U1 shows for knee endoprosthesis surgery.

For dental implantology, it is practical to consider a face-milling cutter that has an underside cutting surface, thereby making it possible to produce a hollow space above the cavity created for the implant, which hollow space has a greater diameter than the cavity. In this connection, the implant inserted and screwed into the cavity projects into the hollow space, so that the bone substitute material according to the invention can be disposed around the upper region of the implant. The bone substitute material, which is preferably disposed flush around the implant, in ring shape, thereby forms a force-bond and shape-bond connection with the implant, as well as after incorporation with the surrounding bone. Claim 6 therefore provides that the bone substitute material is configured in ring shape.

A practicable variant of the invention provides that the set has a drill milling cutter as a surgical instrument. The use of drill milling cutters in dentistry is known. DE 35 43 737 A1 discloses a drill milling cutter for root treatment. The use of a drill milling cutter has the advantage that the production of the cavity for the implant and the production of the hollow space for the bone substitute material can be carried out in one work step.

Furthermore, the invention provides a dental implant that is provided with a bone substitute material composed of granulate, wherein the bone substitute material is of a solid and hard consistency. Also provided is a one-part structure that is composed of the implant and the bone substitute material. Additionally, the implant can preferably be provided with a solid and hard membrane. In this connection, all the components, i.e. implant, bone substitute material, and implant can be releasably connected with one another.

Finally, the invention also provides the use of the bone substitute material, of the membrane according to the invention, as well as the use of the surface-milling cutter for dental implantology.

Figure 2:
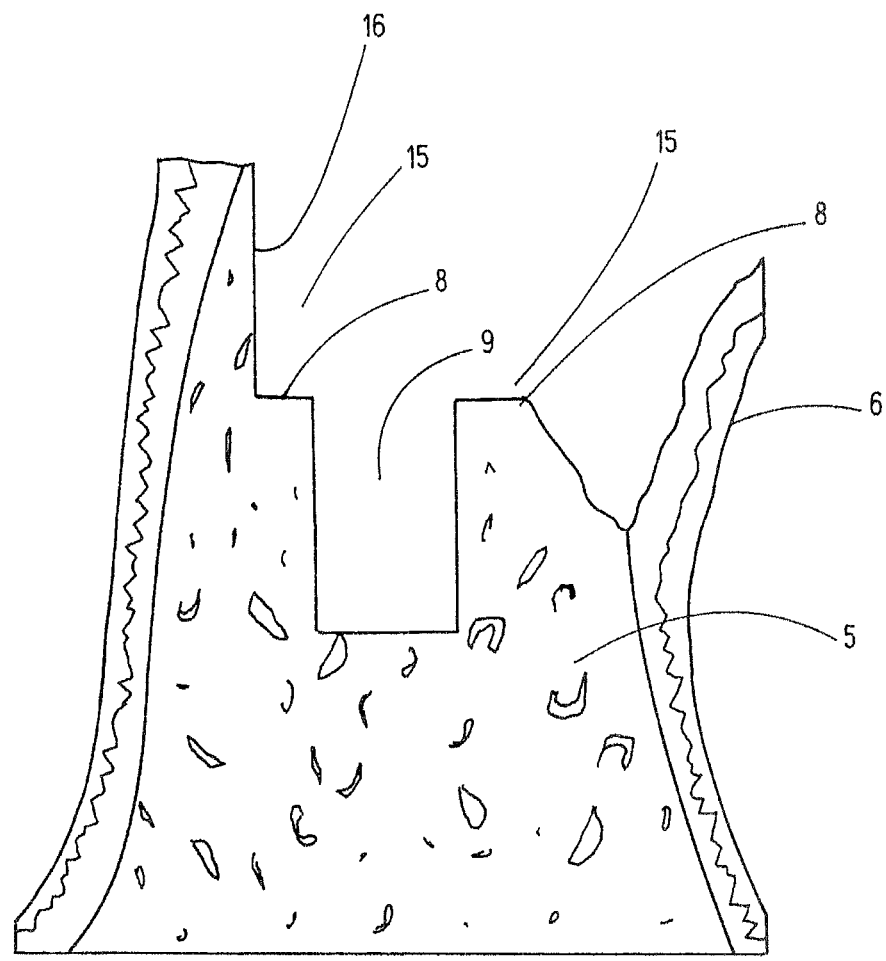
Figure 3:
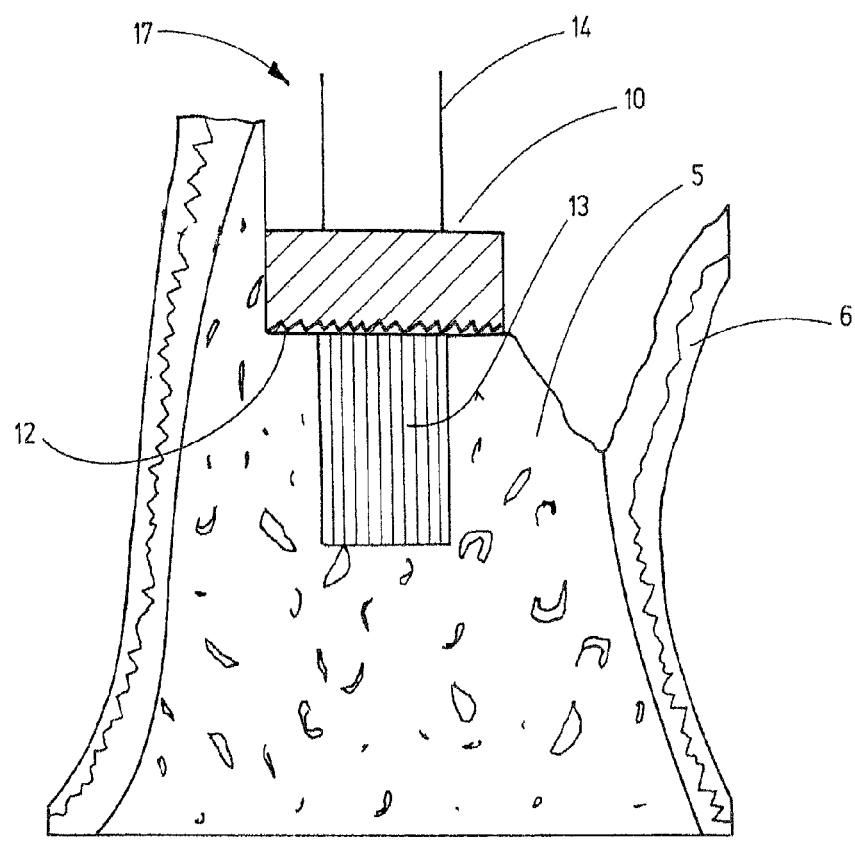
Figure 4:
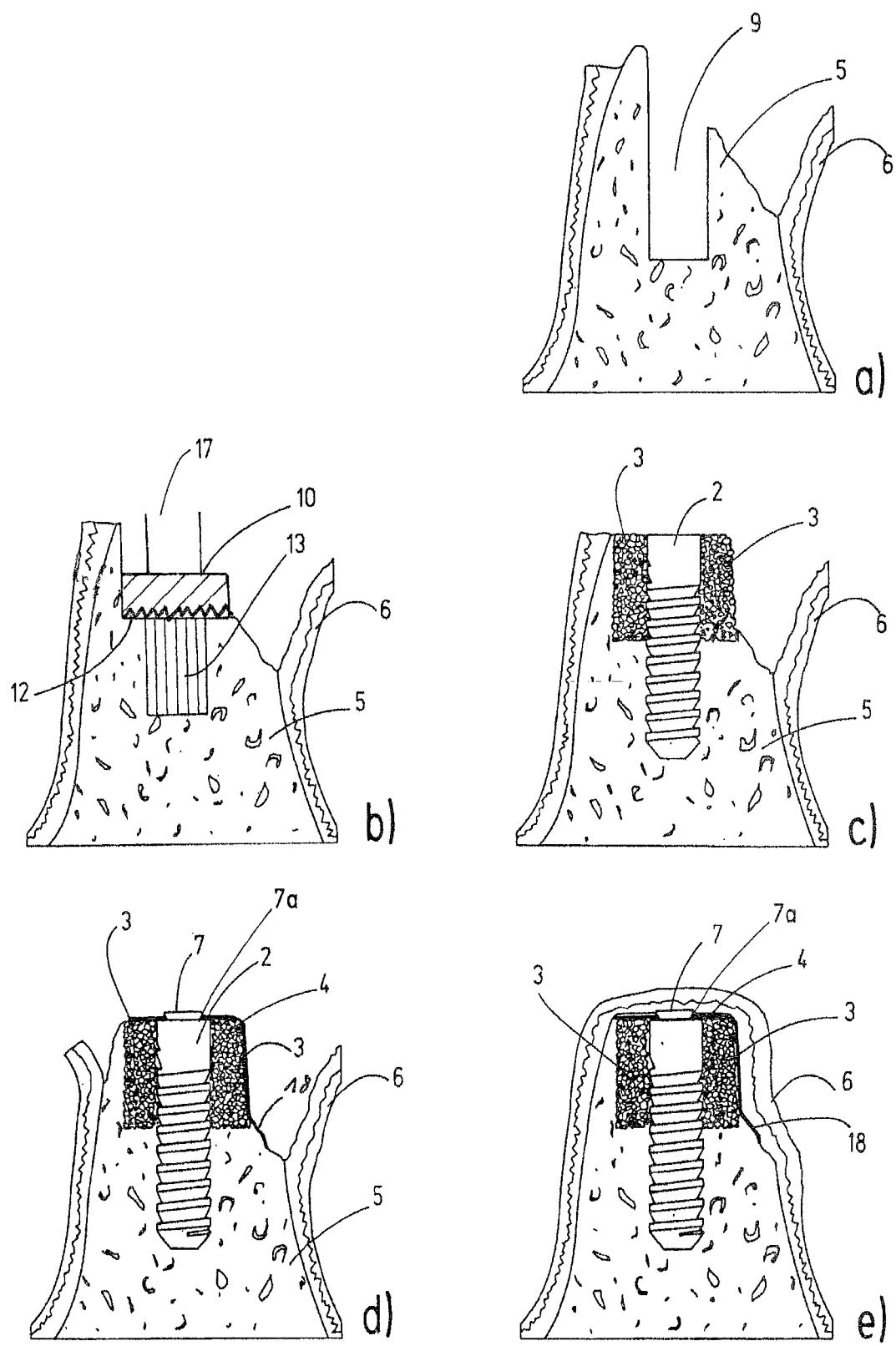

In the following, the invention will be explained in greater detail using the drawings. These show, in a schematic representation:

FIG. 1 in a sectional view, the dental implant set according to the invention, wherein the components of the set are shown after implantation, FIG. 2 in a sectional view, a cavity produced for the implant and a hollow space produced for the bone substitute material, in a jawbone, FIG. 3 in a sectional view, a surface-milling cutter as a further component of the dental implant set according to the invention, wherein the surface-milling is shown during use in dental implantology, and FIG. 4 the steps of dental implantology in a sectional view, in which components of the dental implant set according to the invention are shown.

FIG. 1 shows the dental implant set according to the invention, which is provided with the reference symbol 1 and the components of which are shown in the state of the implant 2 inserted into the toothless region of the jawbone 5 and of the gums 6 sutured above the implant region.

The components of the implant set 1 include, aside from the implant 2, the bone substitute material 3 and the membrane 4. Before insertion of the implant 2, a cavity 9 having a firmly defined and precise width and depth, as is also illustrated by FIG. 2, is produced by means of a conventional implant drill, into which cavity half of the implant 2 is inserted and screwed in, in the embodiment of the invention shown in FIG. 1.

The bone substitute material 3 is disposed around the implant 2, in ring shape. Contrary to the state of the art, the granular bone substitute material 3 is not in a loose, granular state, but rather in a solid and hard state, so that the bone substitute material 3 fills a hollow space 15, previously produced for bone augmentation and shown in FIG. 2, with precise fit, as a ring-shaped, hard block. As is furthermore evident from FIG. 2, the hollow space 15 is delimited, when the gums 6 have been drilled and opened, by a longitudinal side 16 and a shorter side 8, which is formed at the upper end of the cavity 9, so that the cavity 9, in contrast to conventional practice, experiences a spatial expansion, in a way, by means of the hollow space 15, which has a greater diameter than the cavity 9.

The dental implant set 1 according to the invention furthermore has a membrane 4, as FIG. 1 furthermore shows, which membrane, like the bone substitute material 3, is of a solid and hard consistency. The membrane 4, configured in one piece, encloses both the upper face-side end of the implant 2 and of the bone substitute material 3, and a part of the wall of the bone substitute material 3 that is configured as a hard, ring-shaped block, and thereby fits into the upper and lateral outer contour of the bone substitute material 3 and of the implant 2. At the lower end of the part of the membrane 4 that faces the lateral outer contour of the bone substitute material 3, the membrane has a plastically deformable end piece 18, in order to achieve optimal adaptation in the transition from the membrane 4 to the bone 5.

The implant 2 is releasably connected with the membrane 4. For this purpose, the membrane 4 has a hole 7a, and the implant 2 has a snap fastener 7 that corresponds to the hole 7a, so that the membrane 4 can be set onto or pushed onto the implant 2. The snap fastener 7 is part of a closure screw that is an integral component of the implant 2 and with which the upper end of the implant 2 is closed.

FIG. 3 shows a surface-milling cutter 17 in the form of a face-milling cutter as a further component of the dental implantation set 1 according to the invention shown in FIG. 1, specifically during a dental implantation step. The surface-milling cutter 17 has a face-milling cutter element 10 that has a blade 12 on its underside. A centering pin 13 is disposed below and centered relative to the face-milling cutter element 10, the length and depth of which pin correspond to the length and depth of the cavity 9 shown in FIG. 2. As is furthermore evident from FIG. 3, an attachment element 14, which produces the connection with a drive, not shown in FIG. 3, is situated above the face-milling cutter element 10.

Alternatively, instead of the surface-milling cutter 17, a drill milling cutter can also be provided, which has a drill part, in place of the centering pin 13, so that the function of a counter-sinking drill and of a surface-milling cutter are combined in one tool. In this way, the result is advantageously achieved that the production of the hollow space 15 shown in FIG. 2 and the production of the cavity 9 shown in FIG. 2 can be implemented in one work step.

The steps of dental implantation, during which the implant set 1 shown in FIG. 1 as well as the surface-milling cutter 17 shown in FIG. 3 are used, is illustrated by FIG. 4. After the gums 6 have been opened and the cavity 9—as is usual in dental implantology—has been produced by means of a conventional implant drill, as illustrated in FIG. 4a, the surface-milling cutter 17 is used in a next step, shown in FIG. 4b. The diameter of the centering pin 13 of the surface-milling cutter 17 corresponds, in this connection, to the diameter of the cavity 9. The surface-milling cutter 17, which is present in the form of a face-milling cutter, mills the standardized hollow space 15 shown in FIG. 2, by means of the blade 12. Afterward, as FIG. 4c illustrates, the bone substitute material 3, specifically in the form of a ring-shaped block, is inserted into the hollow space 15. Before insertion of the implant 2, the bone substitute material 3 is connected with the implant 2, in non-displaceable manner and in one piece. Alternatively, the bone substitute material 3 can also be inserted into the hollow space 15 shown in FIG. 2 after the implant 2 has been screwed in place, and can be accommodated by the implant 2 and the bone 5. In this connection, a fundamental change in the final bone situation can also be brought about by means of deviating shaping of the bone substitute material 3, specifically in the sense of horizontal and/or vertical bone augmentation.

After the implant 2, which is provided with the bone substitute material 3, has been screwed in, the implant 2 is closed off with a closure screw, which ends with the snap fastener 7 at the top (FIG. 4d).

As is furthermore evident from FIG. 4d, the solid and hard membrane 4 is introduced to cover the implantation region; this membrane is provided with the hole 7a and is buttoned onto the slightly over-contoured edge according to the "snap-fastener" principle. In the transition between bone substitute material 3 covered by the membrane 4 and bone 5, there is the plastically deformable end piece 18 of the membrane 4, in order to achieve optimal adaptation, also with regard to the bone 5.

Finally, as shown in FIG. 4e, the wound is closed by closing and suturing the gums 6.

The present invention is not restricted, in terms of its embodiment, to the preferred exemplary embodiment indicated above. Instead, a number of variants is possible, which make use of the solution presented also for embodiments having a fundamentally different nature. For example, the bone substitute material 3 and the membrane 4 can also consist of materials other than those listed in the specification, or in connection with direct implantation after extraction of a tooth, in which the diameter of the empty tooth socket is greater than the implant diameter.

REFERENCE SYMBOL LIST 1 implant set
2 implant 3 bone substitute material
4 membrane
5 jawbone
6 gums
7 snap fastener
7a hole
8 shorter side
9 cavity
10 face-milling cutter element
12 blade
13 centering pin
14 attachment element
15 hollow space
16 longitudinal side
17 surface-milling cutter
18 end piece

The invention claimed is:

1. A dental implant set comprising:
   an implant,
   a granular bone substitute material, and
   a membrane,
   wherein the granular bone substitute material and the membrane are of a hard and solid consistency and wherein the bone substitute material and the membrane are incompressible.

2. The set according to claim 1, further comprising a surface-milling cutter as a surgical instrument.

3. The set according to claim 1, further comprising a drill milling cutter as a surgical instrument.

4. Set according to claim 2, wherein the milling cutter is a face-milling cutter.

5. The set according to claim 3, wherein the milling cutter has a blade on an underside.

6. The set according claim 1, wherein the bone substitute material is formed in ring shape.

7. The set according to claim 1, wherein the membrane is formed from polylactide.

8. The set according to claim 1, wherein the implant is provided with the bone substitute material.

9. The set according to claim 1, wherein the membrane is provided with a hole.

10. The set according to claim 1, wherein the membrane has a plastically deformable end piece.

11. A bone substitute material composed of granulate, wherein the bone substitute material is of a hard and solid consistency and is not compressible.

12. The material according to claim 11, wherein the material is formed in ring shape.

13. A membrane having a hard and solid consistency, wherein the membrane is incompressible.

14. The membrane according to claim 13, wherein the membrane is provided with a hole.

15. The membrane according to claim 13, wherein the membrane is composed of polylactide.

16. The membrane according to claim 13, wherein the membrane has an elastic end piece.

17. A dental implant provided with a bone substitute material composed of granulate, wherein the bone substitute material is of a hard and solid consistency and is incompressible.

18. The implant according to claim 17, wherein the implant is provided with a hard and solid membrane that is incompressible.

19. The implant according to claim 17, wherein the membrane is releasably connected with the implant.

20. A method for performing dental implantology using the bone substitute material according to claim 11.

21. A method for performing dental implantology using the membrane according to claim.

22. A method for performing dental implantology using the surface-milling cutter according to claim 2.

* * * * *